US005378624A

United States Patent [19]
Berenson et al.

[11] Patent Number: 5,378,624
[45] Date of Patent: Jan. 3, 1995

[54] METHODS FOR REMOVING LIGANDS FROM A PARTICLE SURFACE

[75] Inventors: Ronald J. Berenson, Mercer Island; Dale R. Peterson, Bothell, both of Wash.

[73] Assignee: CellPro, Incorporated, Bothell, Wash.

[21] Appl. No.: 513,056

[22] Filed: Apr. 23, 1990

[51] Int. Cl.$^6$ .............. C12N 1/02; C12N 5/08; C12N 7/02
[52] U.S. Cl. ............... 435/239; 435/240.21; 435/243; 435/254.1; 435/261; 436/541; 436/824; 436/828
[58] Field of Search ............... 530/412, 413, 350, 357, 530/400, 382, 391.1, 391.3; 436/536, 538, 541, 824, 828; 435/261, 254, 243, 240.21, 239, 7.32, 7.31, 7.25, 7.24, 7.22, 7.21, 7.2, 254.1

[56] References Cited

U.S. PATENT DOCUMENTS

| | | | |
|---|---|---|---|
| 4,230,685 | 10/1980 | Senyei et al. | 436/828 |
| 4,276,206 | 6/1981 | Katz | 424/18 |
| 4,416,777 | 11/1983 | Kuroda et al. | 210/446 |
| 4,513,088 | 4/1985 | Lerg et al. | 435/172.2 |
| 4,550,075 | 10/1985 | Barquet et al. | 435/188 |
| 4,714,680 | 12/1987 | Civin | 435/240.25 |
| 4,798,795 | 1/1989 | Sigler | 424/88 |
| 4,935,339 | 6/1990 | Zahradnik | 436/513 |
| 4,965,204 | 10/1990 | Civin | 435/240.27 |
| 5,006,464 | 4/1991 | Chu et al. | 436/531 |
| 5,081,030 | 1/1992 | Civin | 435/240.2 |
| 5,215,927 | 6/1993 | Berenson et al. | 436/541 |
| 5,225,353 | 7/1993 | Berenson et al. | 436/541 |
| 5,256,532 | 10/1993 | Melnicoff et al. | 436/71 |
| 5,262,334 | 11/1993 | Berenson et al. | 436/541 |

FOREIGN PATENT DOCUMENTS

WO87/04628 8/1987 WIPO ............ A61M 1/36

OTHER PUBLICATIONS

Weber et al., J. Chromatog., vol. 431, No. 1, pp. 55-63 (1988).
Updyke et al., Immunochem. Tech. Part 1, pp. 717-725 (1986).
Berenson et al., J. Immunological Methods 91:11-19, 1986.
Norton and Williams, Bio Techniques 96-100, Jun. Jul. 1983.
Thomas et al., J. Immunological Methods 120:221-231, 1989.
Wysocki and Sato, "Method for separating B and T lymphocytes based upon their adherence to polystyrene dishes which have been coated with antibodies specific for cell surface antigens," Proc. Natl. Adac. Sci. USA 75(6):2844-2848, 1978.
Jasiewicz et al., "Selective adsorption of biotin-labelled cells onto avidinated nylon mesh," Exp. Cell Res. 100:213-217, 1976.
Edelman and Rutishauser, "Coupling Reactions and General Methodology," Chapter 15, pp. 195-225.
Fredrickson and Basch, "L3T4 antigen expression by hemopoietic precursor cells," J. Exp. Med. 169:1473-1478, 1989.
Spangrude et al., "Purification and characterization of mouse hematopoietic stem cells," Science 241:58-62, 1988.
Civin et al., "Cell surface antigens on human marrow cells," Int'l J. Cell Cloning 5:267-288, 1987.

(List continued on next page.)

Primary Examiner—Jeffrey E. Russel
Attorney, Agent, or Firm—Seed & Berry

[57] ABSTRACT

A method is provided for removing a second ligand from a particle surface without substantially affecting the particle surface, comprising the step of exposing the particle to a first ligand immobilized onto a support, wherein the particle is exposed under conditions and for a residence time sufficient to allow the second ligand to desorb from the particle surface, and wherein the first ligand has an affinity for the second ligand that is at least two orders of magnitude greater than the affinity of the second ligand for the particle surface, such that the second ligand is removed from the particle surface without substantially affecting the particle surface.

8 Claims, No Drawings

OTHER PUBLICATIONS

Berman et al., "Expression of the Thy-1.2 antigen by Thy-1.1 BW5147 lymphoma cells transfected with unfractionated cellular DNA," *Proc. Natl. Acad. Sci. USA* 81:7176–7179, 1984.

Basch et al., "Hematopoietic thymocyte precursors, and further provides methods for their partial purification," *J. Exp. Med.*, pp. 1843–1848, 1978.

Basch et al., "Antigen SC-1 which can be found on murine multipotential hematopoietic stem cells," *Journal of Cellular Physiology* 107:379–384, 1981.

Beverly et al., "Isolation of human haematopoietic progenitor cells using monoclonal antibodies," *Nature* 287:332–333, 1980.

Olson et al., "Dissociation kinetics of antigen-antibody interactions," *Molecular Immunology* 26(2):129–136, 1989.

Wilchek and Bayer, "Avidin-biotin complexes and their bioanalytical applications," *Analytical Biochemistry* 171:1–32, 1988.

Updyke and Nicolson, "Immunoaffinity isolation of membrane antigens with biotinylated monoclonal antibodies and streptavidin-agarose," *Methods in Enzymology* 121:717–725, 1986.

Fuccillo, "Applications of avidin-biotin techniques," *BioTechniques* 3(6):491–501, 1985.

Korpela et al., "Binding of avidin to the outer membrane porin of *E. coli*," *FEMS Microbiology Letters* 22:3–10, 1984.

Björck and Kronvall, "Protein G, and IgG-binding reagent," *Journal of Immunology* 133(2):969–974, 1984.

Wormmeester et al., "Immunoselective cell separation method wherein biotinylated antibodies and avidin-coupled sheep erythrocytes from rosettes which are separated by density gradient centrifugation," *Journal of Immunological Methods* 67:389–394, 1984.

Kumar and Lykke, "Methods for separating cells based upon various functional characteristics," *Pathology* 16:53–62, 1984.

Basch et al., "Cell separation techniques which utilize positive immunoselection," *Journal of Immunological Methods* 56:269–280, 1983.

Bonnafous et al., "A method for cell separation by affinity chromatography utilizing cleavable mercury-sulfer bonds," Journal of Immunology Methods 58:93–107, 1983.

Fong, "Separation of lymphoid cells on plates which have been coated with ligands, such as a monoclonal antibody," Cell Separation: Methods and Selected Applications 2:203–219, 1983.

Lakow and Basch, "A method for identifying and isolating large numbers of cells using antibody-enzyme complexes," *Journal of Immunological Methods* 44:135–151, 1981.

Berman and Basch, "The use of biotin-avidin to amplify an imunofluorescence signal," *Journal of Immunological Methods* 36:335–338, 1980.

Bayer and Wilchek, "The use of the avidin-biotin complex in molecular biology," *TIBS* (257):377, 1978.

Bayer and Wilchek, "The use of avidin-biotin complexes in molecular biology," Dept. of Biophysics, The Weizmann Institute of Science, Rehovot, Israel, 1–45.

Ghetie et al., "Separation of cells by affinity chromatography on a sepharose gel," *Journal of Immunology Methods* 21:133–141, 1978.

Wigzell, "Affinity cell separation of lymphocytes with antigens which have been coated onto glass or plastic beads in a column," *Scand. J. Immunol.* 5:23–30, 1976.

Kiefer, "Methods for releasing cells which are bound to a nylon mesh," *Eur. J. Immunol.* 5:624–627, 1975.

Schlossman and Hudson, "An immunoabsorbent which can be enzymatically digested to release bound cells," *Journal of Immunology* 110(1):313–315, 1973.

Wigzel and Andersson, "Separation of cells based upon their adherence to antigen-coated columns," Department of Tumor Biology, Karolinska Institute, Sweden, pp. 23–36, 1968.

METHODS FOR REMOVING LIGANDS FROM A PARTICLE SURFACE

DESCRIPTION

1. Technical Field

The present invention relates generally to methods for removing ligands which are bound to the surface of a particle.

2. Background of the Invention

There are many circumstances in which it is desirable to remove a ligand from a cellular surface. For example, in order to sort cells with a Fluorescence-Activated Cell Sorter (FACS), cells must first be labeled with a ligand such as a fluoresceinated monoclonal antibody. Once tagged cells have been sorted, they may be used within biological assays. Binding of an antibody to a cell, however, may cause steric interference or a change in cell behavior. For example, binding of anti-CD3 antibody leads to activation of T cells and hence a change in their behavior (see Fox et al., "Regulation of the Alternative Pathway of T Cell Activation by Anti-T3 Monoclonal Antibody," *J. Immunology* 136:1945, 1986).

Similar problems with cell bound antibodies may be found in cells which are used for therapeutic purposes. Cells which have been labeled with an antibody may traffic differently in vivo, and may trigger an immune response such as antibody-dependent cell cytolysis (Perimann, "Cytotoxic Effects of Lymphoid Cells In Vivo," *Adv. in Immun.* Volume 11, Academy Press, 1969).

It is also desirable to remove ligands other than antibodies from a cell surface. For example, growth factors such as IL-2 or GM-CSF may be used in order to grow cells for a study, but may themselves interfere with the purpose of the study. For example, cells which are grown with IL-2 do not give normal Con-A suppressor activity (see Palacios and Moller, "T Cell Growth Factor Abrogates Concanavalin-A Induced Suppressor Cell Function," *J. Exp. Med.* 153:1360, 1981).

The present invention provides a method for removing a ligand from a particle surface. This method overcomes the disadvantages of prior methods, and further provides other related advantages.

SUMMARY OF THE INVENTION

Briefly stated, the present invention is directed toward methods for removing a second ligand from a particle surface without substantially affecting the particle surface. In one aspect, the method comprises exposing the particle to a first ligand immobilized onto a support, wherein the particle is exposed under conditions and for a residence time sufficient to allow the second ligand to desorb from the particle surface, and wherein the first ligand has an affinity for the second ligand that is at least two orders of magnitude greater than the affinity of the second ligand for the particle surface, such that the second ligand is removed from the particle surface without substantially affecting the particle surface. Within the context of the present invention, the particle may be selected from the group consisting of viruses, bacteria, fungi, parasites, and cells. The method may further comprise, subsequent to the step of exposing, agitating the support upon which the first ligand is immobilized.

Within one embodiment of the present invention, the first ligand is avidin and the second ligand is a biotinylated molecule such as biotinylated transferrin, biotinylated IL-2, a biotinylated anti-particle-surface antibody, or an anti-particle-surface antibody which is coupled to a biotinylated anti-immunoglobulin antibody.

Within another embodiment of the present invention, the first ligand is an anti-immunoglobulin antibody and the second ligand is an anti-particle-surface antibody. Within yet another embodiment of the present invention the first ligand is either protein A or protein G and the second ligand is an anti-particle-surface antibody.

These and other aspects of the present invention will become evident upon reference to the following detailed description.

DETAILED DESCRIPTION OF THE INVENTION

As noted above, the present invention provides methods for the removal of ligands from particle surfaces. Many particles may be utilized within the context of the present invention, including among others, viruses, bacteria, fungi, parasites and cells. Cells include, among other types of cells, classes of human cells such as endothelial cells, tumor cells, pancreatic islet cells, macrophages, monocytes, NK cells, B lymphocytes, T lymphocytes, and hematopoietic stem cells. Representative T lymphocytes include CD4+ cells. CD+8 cells, and specific subsets, such as IL-2R+, CD19+, and transferrin receptor (TrR)+ cells. Hematopoietic stem cells include cells with differentiation markers such as CD34.

The ligand which is bound to the particle surface is referred to as the second ligand. The present invention provides methods for the removal of the second ligand from the particle surface by exposing the particle to a first ligand immobilized onto a support, wherein the particle is exposed under conditions and for a residence time sufficient to allow the second ligand to desorb from the particle surface. Within the present invention, the first ligand has an affinity for the second ligand that is at least two orders of magnitude greater than the affinity of the second ligand for the particle surface, such that the second ligand is removed from the particle surface without substantially affecting the particle surface.

The second ligand is bound to the particle surface prior to the methods of the present invention (see related application entitled "Immunoselection Device and Method," U.S. Ser. No. 07/513,543, filed Apr. 23, 1990, now abandoned, and related application entitled "A Method for Enriching Fetal Cells from Maternal Blood," U.S. Ser. No. 07/513,057, filed Apr. 23, 1990, now abandoned, both of which are incorporated herein by reference). Briefly, the particles are incubated with a second ligand under conditions which permit binding of the ligand to the particle surface. Such incubations are performed to label cells for FACS analysis or fluorescence microscopy, to stimulate or suppress cell behavior, or in preparation for affinity purification. Second ligands which may be removed from a particle surface without substantially affecting the particle surface include receptor substrates to cell surface receptors. For example, lymphokines such as IL-1α, IL-1β, IL-2, IL-3, IL4, IL-5, IL-6, IL-7, GMCSF, G-CSF, M-CSF, IFN-α, IFN-γ, TNF-α, TGF-B, and their respective cell surface receptors are suitable for use within the present invention and are well known in the art.

Many other receptor substrates and their respective particle surface receptors may also be utilized, the choice of second ligand being dependent upon the target particle of interest. The binding of the second ligand to the particle is usually dependent on certain moieties or substrates which are present on the particle. Suitable second ligand-particle substrate pairs include: lectin-carbohydrate (for example, wheat germ agglutinin—N-acetyl glucosamine; and concanavalin A—glucose or mannose); enzyme inhibitor-enzyme (for example, organophosphate-acetyl cholinesterase); binding protein-receptor (for example, fibronectin-gplc, or collagen-gpla); substrate molecule transport protein (for example, cyclophosphamide—multi-drug resistance protein); hormone-receptor (for example, transferrin-transferrin receptor); and vitamin-binding protein (for example, biotin-avidin).

Other second ligands which may be removed from a particle surface include antibodies to particle surface determinates. For example, a monoclonal antibody suitable for use within the present invention may be made according to the method of Hansen et al. (*Immunogenetics* 10:247–260, 1980), or purchased from a conventional source such as the American Type Culture Collection, Rockville, Md. (see ATCC Nos. HB55, HB96, and HB104) and utilized to bind Ia bearing cells. As one of ordinary skill in the art will appreciate, an entire antibody need not be bound to the particle surface. More specifically, only the binding region of the antibody is necessary to specifically bind to the particle surface. Thus, antibody fragments such as Fab or F(ab')₂ fragments, or artificially constructed proteins with incorporated antibody binding proteins (see Reichmann et al., "Reshaping Human Antibodies for Therapy," *Nature* 332:323–327, 1988; Verhoeyen et al., "Reshaping Human Antibodies: Grafting an Antilysozyme Activity," *Science* 239:1534–1536, 1989; and Roberts et al., "Generation of an Antibody With Enhanced Affinity and Specificity for its Antige by Protein Engineering," *Nature* 328:731–734, 1987) may also be removed from a particle surface within the present invention.

The second ligand may also be a complex, for example, a biotinylated receptor substrate, a biotinylated antibody, or a biotinylated antibody coupled to an anti-particle surface antibody. Representative complexes include biotinylated transferrin, biotinylated IL-2, a biotinylated anti-particle-surface antibody, or an anti-particle-surface antibody which is coupled to a biotinylated anti-immunoglobulin antibody. Similarly, avidinated complexes such as an avidinated receptor substrate, an avidinated antibody, or an avidinated antibody coupled to an anti-particle surface antibody may be utilized. Many such complexes may be constructed sufficient for use within the present invention, as long as all of the binding affinities within the second ligand complex are at least two orders of magnitude greater than the affinity of the second ligand for the particle surface.

The first ligand is also selected such that it has an affinity for the second ligand of at least two orders of magnitude greater than the affinity of the second ligand for the particle surface. Choice of the first ligand is dependent on the second ligand. For example, if the second ligand has been biotinylated, avidin may function as the first ligand and be immobilized onto a support. Alternatively, if the second ligand has been avidinated, biotin may function as the first ligand and be immobilized onto the support. If the second ligand is an antibody, protein A, protein G, or an anti-immunoglobulin antibody may be immobilized onto the support and thus function as a first ligand.

Various supports may be used to immobilize the first ligand including, among others, hollow fibers (Andcon Corporation, Danvers, Mass.), beads (Polysciences, Warrington, Pa.), magnetic beads (Robbin Scientific, Mountain View, Calif.), plates, dishes and flash (Corning Glass Works, Corning, N.Y.), meshes (Beeton Dickinson, Mountain View, Calif.), screens and solid fibers (see Edelman et al., U.S. Pat. No. 3,843,324; see also Kuroda et al., U.S. Pat. No. 4,416,777), membranes (Millipore Corp., Bedford, Mass.), and dipsticks. A variety of different sources exist for supports other than those designated. Particularly preferred is a support such as Biogel P-60 TM (BIORAD, Richmond, Calif.). Biogel P-60 TM is a porous polyacrylamide hydrogel bead. The beads are generally spherical, on average about 250 microns in size, and have an average pore size which excludes molecules larger than approximately 60,000 daltons.

Many methods may be used to immobilize the first ligand onto the support. For example, a ligand, such as an antibody, may be directly coupled to the support by various methods (see J. K. Inman, *Methods In Enzymology*, Vol. 34, *Affinity Techniques, Enzyme Purification: Part B*, W. B. Jakoby and M. Wilchek (eds.), Academic Press. New York, p. 30, 1974; see also M. Wilcheck and W. Bayer, "The Avidin-Biotin Complex in Bioanalytical Applications," *Anal. Biochem*, 171:1–32, 1988). These methods include the use of glutaraldehyde, carbodiimide, carbonyl diimidazole, cyanogen bromide, tosyl chloride, biotin/avidin, and biotin/streptavidin.

As noted above, the particle is exposed to the immobilized first ligand under conditions, and for a residence time sufficient to allow the second ligand to desorb from the particle surface, such that the second ligand is removed from the particle surface without substantially affecting the particle surface. Within the context of the present invention, sufficient "residence time" for the second ligand to desorb from the particle surface and bind to the first ligand may be mathematically represented as $$t \geq \frac{0.9}{k \times P}$$

where
- t = required residence time
- k = the first order dissociation rate constant for the second ligand from the particle surface.
- P = probability of binding to a first ligand site as defined by the equation below:

$$P = \frac{L/r_L^2}{L/r_L^2 + C/r_c^2}$$

where
- L = # first ligand sites
- C = # cell surface sites
- $r^2$ = average distance squared to site.

The dissociation constant for a second ligand desorbing from a surface can be readily measured using radiolabeled second ligand according to the method of Olson et al. ("Dissociation Kinetics of Antigen-Antibody interactions: Studies on a Panel of Anti-Albumin Monoclonal Antibodies," *Molecular Immunology*

26:129–136, 1989). Briefly, the particle surface is first saturated with second ligand, a proportion of which is radiolabeled. The surface is then placed in fresh solution containing second ligand which is not radiolabeled. The rate of appearance of radiolabeled second ligand in the fresh solution can be used to calculate the rate constant for dissociation of second ligand from the particle surface. The other variables may also be readily determined. For example, the number of cell surface sites may be determined through the use of a radiolabeled antibody, or by quantitative FACS analysis, and the number of avidin sites may be measured with radiolabeled biotin. The "average distance squared to site" may be calculated by squaring the distance between the ligand and each respective site, summing the squared distances over the total number of sites, and dividing by the number of sites.

As noted above, the second ligand is removed from the particle surface without substantially affecting the particle surface. Through use of the present invention at least 25%, and preferably 70% to 90% of the second ligand is removed from the particle surface. Furthermore, within the context of the present invention, a particle surface is not "substantially affected" if greater than 90% of the cell surface antigens or receptors remain. This determination may be easily accomplished through many different techniques. For example, cells which were labeled with biotinylated IL-2 may be passed through an avidin-coated support material in order to remove the bound IL-2. The cells may then be labeled with a fluorescein-labeled anti-IL-2 receptor antibody and analyzed by FACS to determine if the intensity of fluorescence staining is within 90% of the fluorescence intensity of starting cells which were never exposed to the biotinylated IL-2.

Within one aspect of the present invention, subsequent to the step of exposing the particle to the first ligand, the support upon which the first ligand is immobilized is agitated. Within a preferred embodiment, a support such as Biogel ™ beads with an immobilized first ligand are contained within a column. Also contained within the column is a means for agitating the beads. The particle with bound second ligand is exposed to the immobilized first ligand, resulting in the binding of the first ligand to the second ligand, hence immobilizing the particles. Upon application of an external force, the means for agitation agitates the beads. The weakest bonds are disrupted first; since the affinity of the first ligand for the second ligand is at least two orders of magnitude greater than the affinity of the second ligand for the particle surface, the particle—second ligand bond will be disrupted first, removing the second ligand from the particle surface.

Means for agitating the support include magnetic impellers (Parker Industries Corporation, Chicago, Ill.), magnetic beads (Robbin Scientific, Mountain View, Calif.), weights (Astrolite Alloys, Camarillo, Calif.), magnetic weights, pipettes, and buoyant floats (Polysciences Corp., Warrington, Pa.). The external force which supplies energy to the means for agitating the support is generally located outside of the column and includes electromagnetic, gravitational and mechanical forces. Electromagnetic forces may act on means such as metallic or magnetic beads or weights, causing agitation and release of particles. Electromagnetic forces may be provided by, for example, magnetic stir plates (VWR Scientific, San Francisco, Calif.) or electromagnetic coils (Radio Shack). Gravitational forces may be provided by, for example, rocking plates or manual shaking of a column, such that the forces of gravitation agitate the support, thereby causing release of particles. A weight which is either denser or more buoyant than the support may be placed in the bed to enhance the effect of gravitational forces on bed agitation. Mechanical forces may be provided by, for example, hydrodynamic jets (VWR Scientific, San Francisco, Calif.), vortexes (VWR Scientific, San Francisco, Calif.), or sonicators (Curtin Matheson Scientific, Seattle, Wash.). To determine the proper level of agitation using these means, the level of force is gradually increased until the support is visibly moved. This level of agitation may then be fine-tuned (e.g., a lower force to remove only nonspecifically bound particles, or a higher force to remove the most tightly bound particles) to fit the specific application.

The following examples are offered by way of illustration and not by way of limitation.

EXAMPLES

Example 1

Carboxylation of a Polyacrylamide Gel

Seventeen grams of dry Biogel P-60 ™, (50–100 mesh (wet), coarse beads) (BIORAD, Catalog No. 150-1630, Richmond, Calif.) are added to 1.5 l of 0.5M $NaHCO_3$/0.5M $Na_2CO_3$. The pH is adjusted to 10.5 with NaOH and carefully stirred with a mixer (RZR1, Carfamo, Wiarton, Ontario, Canada) so as not to damage the beads for approximately 20 to 30 minutes. The mixture is then placed in a 60° C. water bath. After the mixture reaches a temperature of 60° C., it is incubated for an additional 2 hours (at 60° C.) with occasional stirring. The mixture is then removed from the water bath, and placed in an ice bath to bring the mixture temperature down to room temperature.

The beads are washed several times with distilled or deionized water, followed by several washings of PBS using a coarse glass filter connected to a vacuum. The carboxylated gel may be stored in PBS at 4° C., and is stable for up to one year if sterilized or stored with a preservative.

Example 2

Avidin Conjugating the Carboxylated Biogel

PBS is first removed from a measured amount of carboxylated Biogel by filtering with a coarse glass filter connected to a vacuum. The gel is then equilibrated in distilled or deionized water for 15–30 minutes. Equilibration in water causes an expansion of the gel to a volume of about 4 times its previously measured amount. The gel is resuspended in 10 ml of distilled or deionized water for each ml of gel (as originally measured in PBS).

Ten mg of 1-ethyl-3-(3-dimethylaminopropyl) carbodiimide (EDC-HCl) (Sigma Chemical Co., Catalog No. E7750, St. Louis, Mo.) is added for each ml of gel as originally measured. The pH is rapidly adjusted to 5.5 by dropwise addition of HCl. Care is taken to maintain the pH at 5.5; pHs of less than 5.0 or greater than 6.0 result in significantly less activation of the Biogel. The mixture is stirred for five minutes.

Avidin (International Enzymes, Inc., Fallbrook, Calif.) is dissolved at a concentration of between 10 and 100 mg/ml in deionized water. Next, 100 μg of avidin is rapidly added for each ml of gel (as originally measured in PBS). The mixture is stirred for 1.5 hours. Next, 2M glycine is added to give a final concentration of 0.2M glycine in the mixture, and stirred for an additional 1 hour.

The gel is washed with several volumes of PBS using a coarse glass filter and vacuum, and stored in PBS with 0.1% NaN$_3$ at 4° C. The gel is stable for approximately one year.

Example 3

Removal of Biotinylated Anti-Ia Antibody From Daudi Cells

A. PREPARATION OF CELLS

Daudi cells (ATCC No. CCL 213) are centrifuged at 280 g for 8 minutes and resuspended in PBS+1% BSA at $1 \times 10^8$ cells/ml. The cells are incubated with biotinylated anti-Ia antibody at a concentration of 2.5 µg/ml for 30 minutes at 4° C. The cells are resuspended in PBS+1% BSA after the first spin, then resuspended in PBS+5% BSA to a concentration of $5 \times 10^7$ cells/ml following the second spin.

p B. AVIDIN COLUMN PREPARATION

Carboxylated Biogel P-30 ™ (prepared as described above) is allowed to equilibrate to room temperature and placed in a K9/15 column (Pharmacia, Piscataway, N.J.) to a total bed height of 1 cm. The column is washed with PBS, followed by washes with PBS plus 5% BSA. This column functions as a "pre-column." The avidin column contains avidin-conjugated Biogel P-60 ™, which is prepared as described above. The avidin-conjugated Biogel is allowed to equilibrate to room temperature, and placed in a K9/15 column to a total bed height of 4 cm. The column is then washed with several volumes of PBS, followed by washes with PBS plus 5% BSA.

C. IMMUNOADSORPTION OF CELLS

Cells which have been prepared as described above are gently transferred onto the top of the gel bed of the pre-column. The cells are allowed to filter through the pre-column and are washed with 1 ml PBS plus 5% BSA into the avidin column. A peristaltic pump (Cole-Parmer, Rockford, Ill.) controls flow from the avidin column to a rate of about 1 ml/minute. Once the cells have almost all entered the top of the avidin column bed, 1–2 ml of PBS plus 5% BSA is added to the top of the avidin column in order to wash out remaining cells. The column is washed out with 4–6 ml of PBS.

D. REMOVAL OF ADSORBED CELLS FROM THE AVIDIN COLUMN

The avidin column is placed on top of a 15 ml centrifuge tube. The valve of the column is opened and 15 ml of PBS is added to the column with a wide bore, 9-inch transfer pipette. The PBS is added to the column while the pipette is used for mechanically agitating and resuspending the cell bed, thus allowing cells to become detached from the gel matrix, and to filter into the centrifuge tube. The tube is then centrifuged at 280 g for 8 minutes and the pellet is resuspended in Iscoves' Modified Dulbecco's Medium plus 10% Fetal Bovine Serum. The total time of exposure of the cells to the avidin gel is about 15 minutes.

E. RESULTS

The cells are labeled with fluorescein-tagged antibodies and analyzed with a FACScan for fluorescence intensity. The starting cells, nonadherent, and the cells which adhered to the avidin-conjugated Biogel are stained with fluoresceinated goat-anti-mouse IgG (Tago) to determine the amount of anti-Ia antibody remaining on the cell surface. The adherent cells bound 30% and the nonadherent cells bound 25% as much of the goat-anti-mouse FITC as the starting cells, indicating that 70%–75% of the anti-Ia antibody is removed from the cell surface. Next the adherent and starting cells are restrained with a fluoresceinated anti-HLA-dr (Becton Dickinson, Mountain View, Calif.) antibody to determine if the antigen density had been altered. The adherent cells stained 16% brighter than the starting cells indicating that the Ia antigen (HLA-DR molecule) remained on the cells even though the anti-Ia antibody had been removed.

Example 4

Removal of Biotinylated Transferrin From Cell Surface

A. PREPARATION OF CELLS AND COLUMN

CEM cells (ATCC #CCL 119) are centrifuged at 280 g for 8 minutes and $20 \times 10^6$ cells were resuspended in 100 ul of biotinylated transferrin (Terry Fox Laboratory, Vancouver, B.C.) at 0.3 mg/ml for 30 minutes at 4° C. The cells are washed by centrifugation at 280 g for 8 minutes, resuspended in PBS+1% BSA and centrifuged again, then resuspended in PBS+5% BSA to a concentration of $5 \times 10^7$ cells/ml.

A carboxylated Biogel P-30 ™ precolumn and a P60 avidin column are prepared and operated as described above in Example 3.

B. RESULTS

The cells are labeled with fluorescein-tagged avidin (Vector, Burlingame, Calif.) to measure the amount of biotinylated transferrin on the cells. The cells are relabeled with biotinylated transferrin then fluorescein-tagged avidin to measure the amount of transferrin receptors on the cells. The amount of label is then analyzed with a FACScan for fluorescence intensity.

The cells which bind to the column and are agitated off after approximately 15 minutes residence time have lost 87% of the biotinylated transferrin. Those cells which remain on the column for 60 minutes before agitation have lost 90% of the transferrin on their surface. Restaining with biotinylated transferrin, followed by avidin-FITC shows that the cells averaged 97% as many transferrin receptors as the starting cells.

From the foregoing it will be appreciated that although specific embodiments of the invention have been described herein for the purposes of illustration, various modifications may be made without deviating from the spirit and scope of the invention. Accordingly, the invention is not limited except as by the appended claims.

We claim:

1. A method for removing a second ligand from a particle surface, said particle being selected from the group consisting of viruses and cells, without substantially affecting the particle surface, comprising:

exposing the particle to an anti-immunoglobulin antibody which is immobilized onto a support, wherein said particle is exposed under conditions and for a residence time sufficient to allow an anti-particle surface antibody to desorb from the particle surface, and wherein said anti-immunoglobulin antibody has an affinity for the anti-particle surface antibody that is at least two orders of magnitude greater than the affinity of the anti-particle surface antibody for the particle surface, such that the anti-particle surface antibody is removed.

2. A method for removing a second ligand from a particle surface, said particle being selected from the group consisting of viruses and cells, without substantially affecting the particle surface, comprising:

exposing the particle to a first ligand selected from the group consisting of protein A and protein G, which is immobilized onto a support, wherein said particle is exposed under conditions and for a residence time sufficient to allow an anti-particle surface antibody to desorb from the particle surface, and wherein said first ligand has an affinity for the anti-particle surface antibody for the particle surface, such that the anti-particle surface antibody is removed.

3. The method according to claim 1 or 2 wherein said cells are selected from the group consisting of CD4+ cells, CD8+ cells, transferrin receptor+ cells, and CD34+ cells.

4. The method according to claim 1 or 2 wherein said cells are selected from the group consisting of B lymphocytes and T lymphocytes.

5. The method according to claim 1 or 2 wherein said cells are tumor cells.

6. The method according to claim 1 or 2 wherein said cells are selected from the group consisting of bacterial cells and fungal cells.

7. The method according to claim 1 or 2 wherein said cells are parasitic cells.

8. The method according to claim 1 or 2 wherein said cells are human cells.

* * * * *

UNITED STATES PATENT AND TRADEMARK OFFICE
CERTIFICATE OF CORRECTION

PATENT NO. : 5,378,624
DATED : January 3, 1995
INVENTOR(S) : Ronald J. Berenson and Dale R. Peterson It is certified that error appears in the above-indentified patent and that said Letters Patent is hereby corrected as shown below:

In column 8, claim 1, line 57, please delete "a second ligand" and substitute therefor --an anti-particle surface antibody--.

In column 9, claim 2, line 5, please delete "a second ligand" and substitute therfor --an anti-particle surface antibody--.

Signed and Sealed this

Thirteenth Day of February, 1996

Attest:

BRUCE LEHMAN

Attesting Officer

Commissioner of Patents and Trademarks